United States Patent
Boese

(10) Patent No.: US 7,471,760 B2
(45) Date of Patent: Dec. 30, 2008

(54) DEVICE FOR OBTAINING STRUCTURE DATA OF A MOVING OBJECT

(75) Inventor: Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 235 days.

(21) Appl. No.: 11/098,811

(22) Filed: Apr. 5, 2005

(65) Prior Publication Data

US 2005/0226485 A1   Oct. 13, 2005

(30) Foreign Application Priority Data

Apr. 8, 2004   (DE) .................... 10 2004 017 478

(51) Int. Cl.
*G01N 23/00* (2006.01)
*H05G 1/00* (2006.01)

(52) U.S. Cl. .................. 378/8; 378/98.12; 378/165; 382/130

(58) Field of Classification Search .............. 378/4–20, 378/62, 63, 95, 98.11–98.12, 165, 901; 382/128, 382/130–132

See application file for complete search history.

(56) References Cited

U.S. PATENT DOCUMENTS

| | | | |
|---|---|---|---|
| 5,490,221 A | * | 2/1996 | Ransford et al. ............ 382/130 |
| 5,839,440 A | * | 11/1998 | Liou et al. ................... 600/431 |
| 6,295,464 B1 | * | 9/2001 | Metaxas ...................... 600/407 |
| 6,496,716 B1 | * | 12/2002 | Langer et al. ............... 600/425 |
| 6,792,066 B1 | * | 9/2004 | Harder et al. .................. 378/4 |
| 2002/0168095 A1 | * | 11/2002 | Spreeuwers et al. ......... 382/131 |
| 2002/0186871 A1 | | 12/2002 | Grass et al. |
| 2004/0077941 A1 | * | 4/2004 | Reddy et al. ................ 600/428 |
| 2004/0175024 A1 | * | 9/2004 | Rasche et al. .............. 382/128 |
| 2005/0002546 A1 | * | 1/2005 | Florent et al. .............. 382/128 |
| 2005/0113674 A1 | * | 5/2005 | Salla et al. .................. 600/413 |
| 2005/0220264 A1 | * | 10/2005 | Homegger ..................... 378/8 |
| 2006/0023840 A1 | * | 2/2006 | Boese ..................... 378/98.12 |
| 2006/0210019 A1 | * | 9/2006 | Rasche et al. ................. 378/62 |

FOREIGN PATENT DOCUMENTS

WO   WO 02/103639 A2 * 12/2002

* cited by examiner

*Primary Examiner*—Allen C. Ho
*Assistant Examiner*—Anastasia Midkiff

(57) ABSTRACT

In addition to a radiation source (6) attached to a C-arm 4, and in addition to a detector (7), a rotation angiography device (1) for the angiocardiography has an evaluation unit (8), which formulates models with low resolution from the projection images supplied by the detector (7) for the moving object to be examined, and which generates movement fields for the projection images generated by the detector (7) on the basis of the model, so that movement-corrected projection images can be calculated from the projection images, which can be used to formulate a three-dimensional high-resolution model of the object to be examined.

8 Claims, 6 Drawing Sheets

DEVICE FOR OBTAINING STRUCTURE DATA OF A MOVING OBJECT

CROSS REFERENCE TO RELATED APPLICATIONS

This application claims priority to the German application No. 10 2004 017 478.4, filed Apr. 8, 2004 which is incorporated by reference herein in its entirety.

FIELD OF INVENTION

The invention relates to a device for obtaining structure data of a moving object with:
- a radiation source which can be moved about an object along a measurement path;
- a detector arranged on the opposite side of the object and which can be moved according to the movement of the radiation source and,
- an evaluation unit which determines the structure data of the object from the projection images.

BACKGROUND OF INVENTION

A device of this type is generally known from US 2002/0186871 A1 and from the field of three-dimensional angiocardiography. Three-dimensional structure data of the moving heart is obtained in rotation angiocardiography, in which an X-ray source and an X-ray detector rotates about the patient at an angular range greater than 180° and thus records projection images of the moving heart. The structure data of the object can then essentially be determined in the form of three dimensional spacial coordinates from the projection images.

SUMMARY OF INVENTION

One problem here is that the heart of a patient beats multiple times during the long rotation of the X-ray source and X-ray detector which typically takes 3 to 10 seconds. The movement of the heart results in major artifacts during the three-dimensional reconstruction of the structure data of the heart.

Attempts have hitherto been made to solve this problem of angiocardiography in that during the recording of the projection images the relevant phase of the heart movement is determined with the aid of an electrocardiograph. Subsequently fewer projection images are selected from the projection images recorded during a complete rotation, said projection images displaying the heart in a still phase.

This selection results in the substantial deterioration of both the spatial resolution and the contrast resolution of the three-dimensional structure data.

Conversely, it is also possible to extract more projection images for obtaining the structure data but in this case, the temporal resolution deteriorates.

An object of the invention is therefore, using this prior art as a starting point, to create a device with which structure data of a moving object can be obtained with a high spacial and time resolution.

This object is achieved by the claims. Further advantageous embodiments and developments are set down in the dependent claims.

In addition to a radiation source and a detector which move about the object along a measurement path, the device has an evaluation unit in which a moderator from the projection images in various time frames determines an object model valid for the relevant time frame in each instance. A movement analyzer of the evaluation unit can then derive model projection images with the aid of the object model, and determine movement fields for the projection images from the model projection images. A movement compensator in the evaluation unit is thus able to calculate movement-corrected projection images on the basis of the movement field, so that a reconstruction unit of the evaluation unit can finally determine the structure data of the object from the movement-corrected projection images.

The concept behind the invention is that valuable movement information can still be obtained from the object models calculated from the modelator despite the poor local and contrast resolution. Then movement fields of the projection images can be estimated from the different object models assigned to the various time frames. This is possible in particular if the details of the moving object which initially do not appear in the structure object model, move in a similar manner to the associated roughly structured regions of the object to be examined.

A large number of recorded projection images can be used since, with the device for the reconstruction of the structure data, the structure data has an improved local and contrast resolution in comparison with the prior art. It is also possible to achieve a high time resolution as the recorded projection images can essentially be movement-corrected at each time point.

In a preferred embodiment the object to be examined is a cyclically moving object and the device has a movement sensor by means of which the phases of the cycle can be detected. The movement correction is facilitated in this way, since the phases of the cycle do not have to be estimated from the recorded projection images themselves.

If the device is used within the context of angiocardiography for examining a moving heart, the movement sensor is preferably an electrocardiograph.

In a further preferred embodiment, the evaluation unit of the device is designed for an iterative data reduction. In this case, the reconstruction unit creates structure data sets assigned to various time points and the movement analyzer determines refined model projection images from the structure data sets, said model projection images serving to calculate movement fields arranged around addition details for the conventional projection images. The evaluation unit can repeat the data reduction as often as necessary until the calculated structure data sets only change slightly.

BRIEF DESCRIPTION OF THE DRAWINGS

Further features and advantages of the invention are set down in the description below, in which the exemplary embodiments of the invention are described in detail with reference to the accompanying drawing, in which.

DETAILED DESCRIPTION OF INVENTION

Figure 1:
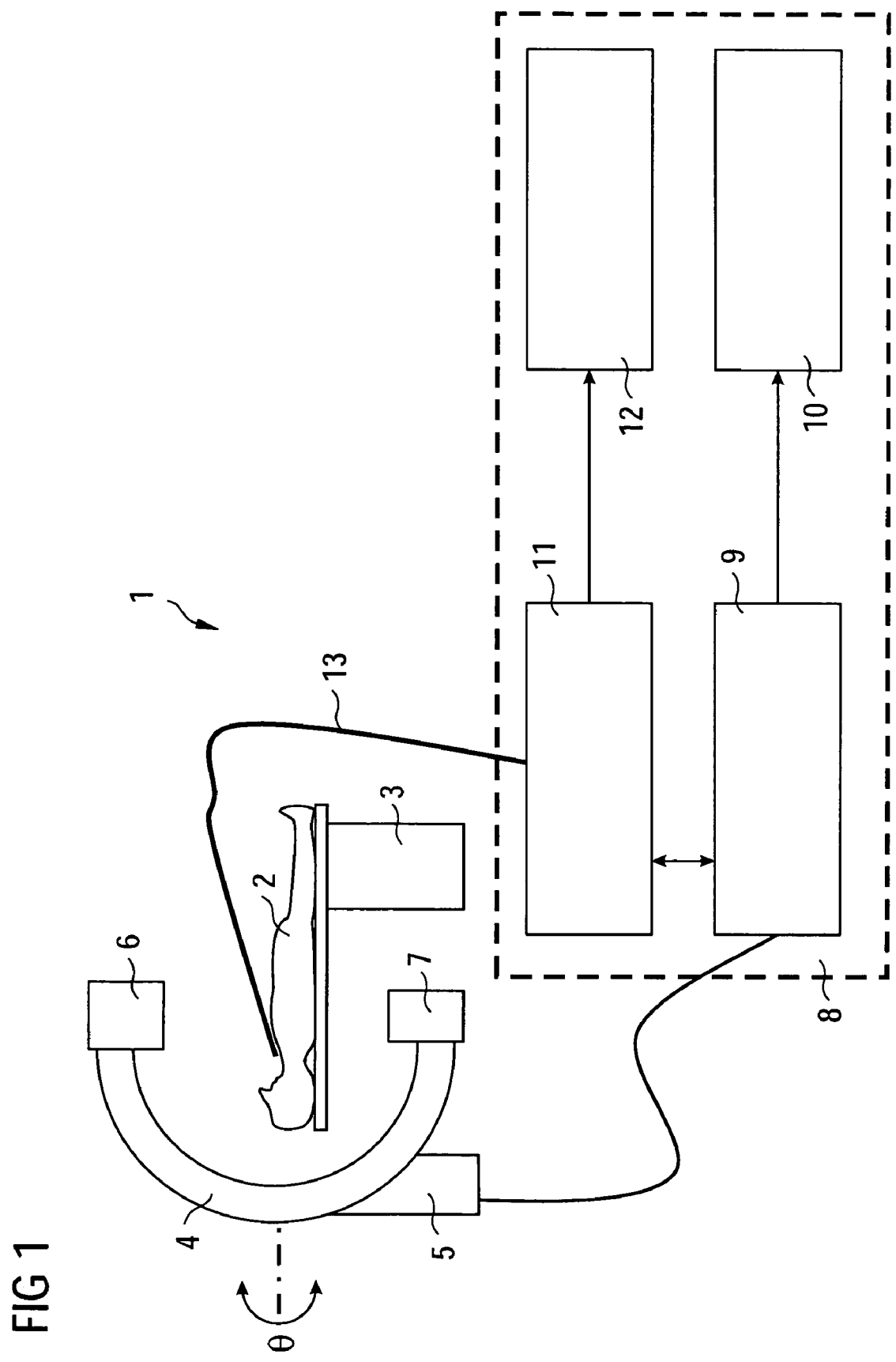
FIG. 1 shows an angiography device for the three-dimensional rotation angiocardiography.

FIG. 1 shows an angiography device 1 which serves to obtain structure data from a heart of a patient 2. This structure data can be a three-dimensional model of the heart of the patient 2. The structure data can also be sections through the heart of the patient 2. Furthermore, the structure data can be obtained with or without time resolution.

The patient 2 typically lies on a table 3, which can be rotated by a C-arm 4. The C-arm 4 is attached to a support 5 which allows the C-arm 4 to rotate about the patient 2. Furthermore, the C-arm 4 has an X-ray source 6 and an X-ray detector 7, which serves to record projection images of the heart of the patient 2. The projection images generated by the X-ray detector 7 are supplied to an evaluation unit 8, which has an image processing unit 9 with connected image memory 10 and an electrocardiograph 11 with a connected heart signal memory 12. The electrocardiograph 11 is connected to the patient 2 by means of electrodes 13.

Figure 2:
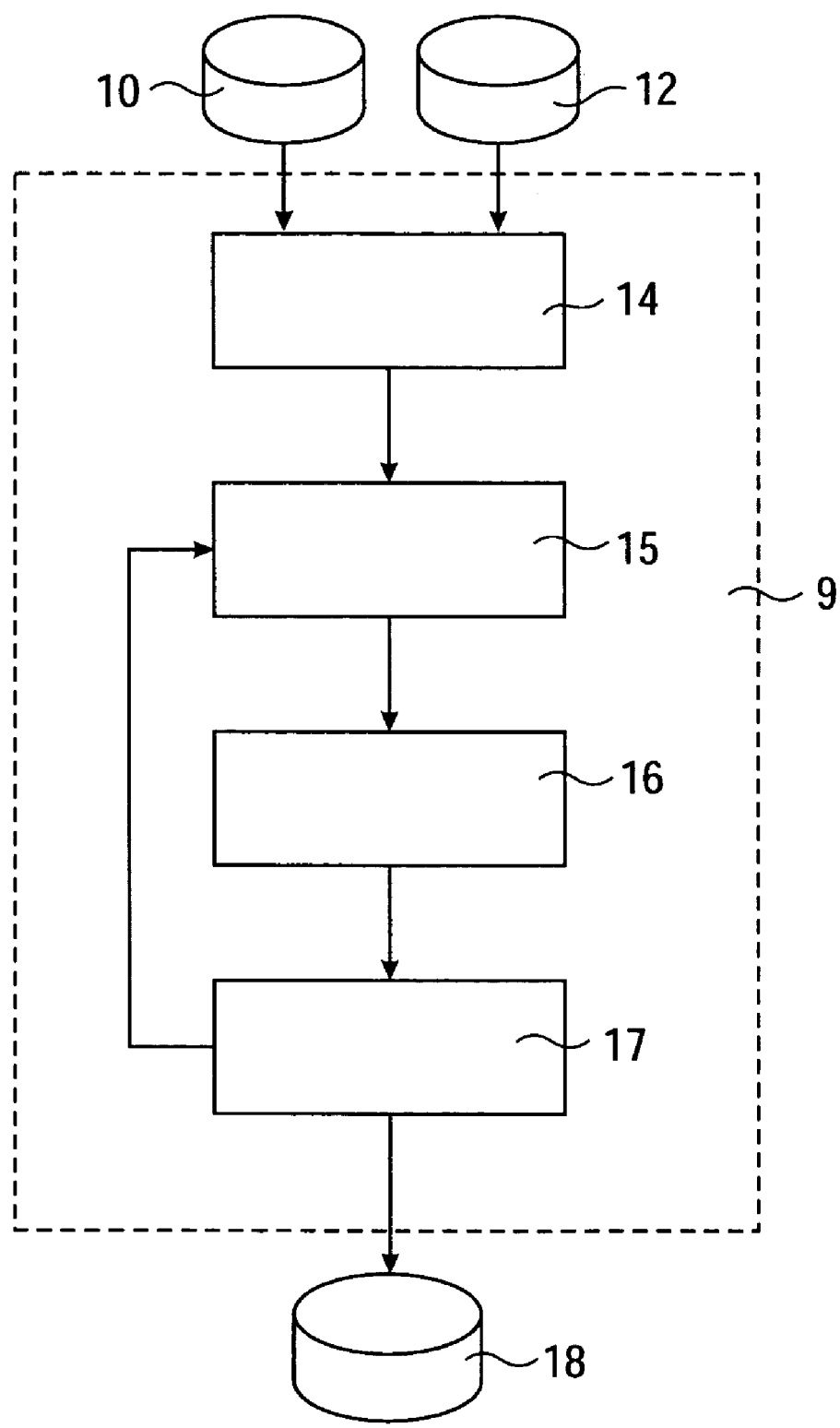
FIG. 2 depicts a logical function unit in an evaluation unit of the angiography device in FIG. 1.

FIG. 2 shows logical function units of the image processing unit 9. The image processing unit 9 has a modelator 14 which generates heart models assigned in each instance to various time frames from the heart signal data stored in the heart signal memory 12 and from the projection images stored in the image memory 10. A movement analyzer 15 determines a series of movement fields with the aid of a model generated by the modelator 14, with the aid of which a movement compensator 16 corrects the movement of the heart in the original projection images. A reconstruction unit 17 determines the structure data of the heart from the movement-corrected projection images from the movement compensator 16, said structure data being stored in a structure data memory 18. In a further iteration of the data reduction, the structure data generated by the reconstruction unit 17 can be made available to the movement analyzer 15, from which it calculates refined movement fields.

The function of the individual logical function units of the image processing unit 9 shown in FIG. 2 is described below in detail.

Figure 3:
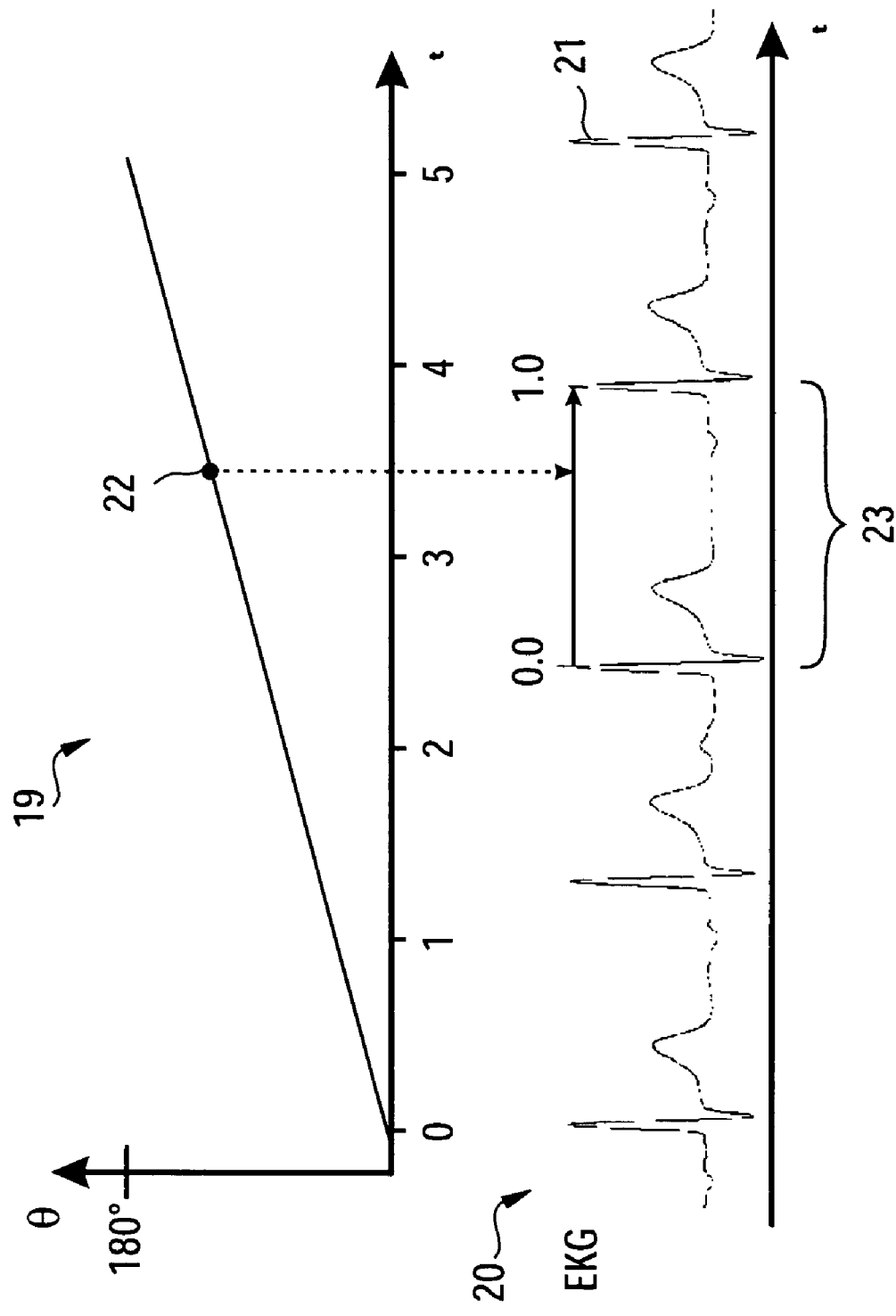
FIG. 3 shows a diagram displaying the temporal development of a projection angle of the angiography device and an electrocardiogram of an examined patient.

FIG. 3 shows a movement diagram 19, in which the projection angle θ of the C-arm 4 is applied against the time t, whilst the C-arm 4 moves about the patient 2. The projection angle increases continuously with time based on the continual movement of the C-arm 4.

Furthermore, FIG. 3 contains an electrocardiogram 20 of a patient 2. The so-called R-jags 21 are clearly noticeable based on which it is possible to assign a heart cycle 23 of the heart of a patient 2 to a rotation status 22 of the C-arm 4. A heart cycle 23 extends in each instance from an R-jag 21 to the next R-jag 21. As the movement of the heart is cyclically repeated, a relative time $t_{rel}$ can be assigned to the movement process of the heart within a cycle, said relative time assuming values between 0 and 1.

It should be noted that the projection angle θ represents the whole set of position data, which completely describes the position of the C-arm 4.

Figure 4:
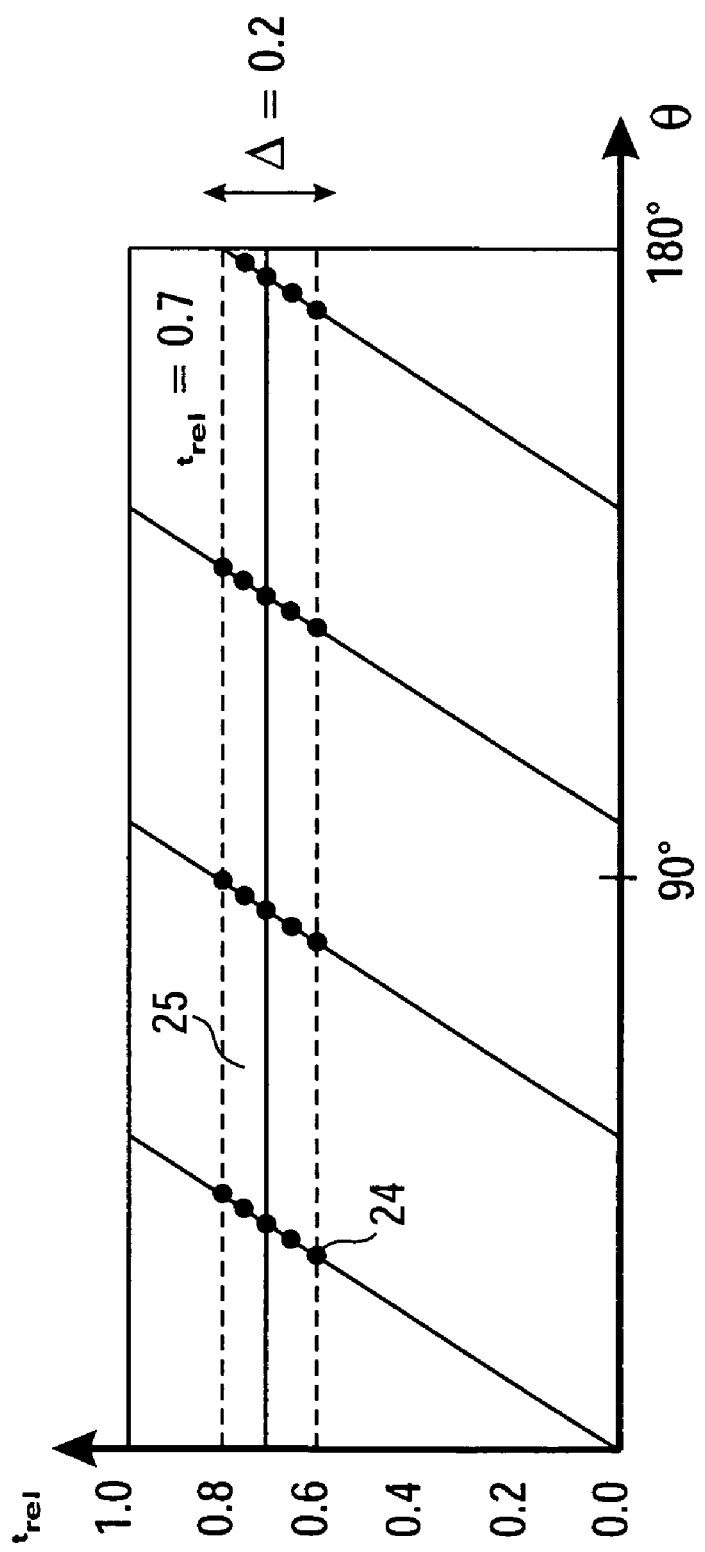
FIG. 4 shows a, diagram in which the phase angle of recorded projection images is displayed in relation to the projection angle of the angiography device and the relative time of a heart cycle.

FIG. 4 now displays a diagram, in which phase angles 24 of the projection images generated by the X-ray detector 7 are plotted in relation to the projection angle θ and the relative time $t_{rel}$.

FIG. 4 particularly displays the phase angles 24 of projection images which lie in a time frame 25, which is centered on $t_{rel}$=0.7 and has a width of Δ=0.2. From the projection images which can be assigned to the time frame 25, the modelator 14 from FIG. 2 now calculates a model for the heart of the patient 2, which is assigned to the relative time $t_{rel}$=0, . This model generally suffers from a poor local and contrast resolution.

In addition, the modelator 14 in further time frames 25 calculates further models of the heart. The phase strips are therefore preferably centered on the relative times $t_{rel}$=0.1/n, 2/n, 3/n ... n-1/n and distributed equally over the heart cycle 23. A value Δ=1/n or greater is chosen as the width of the time window 25, whereby the latter results in a time frame 25 to be overlapped.

Figure 5:
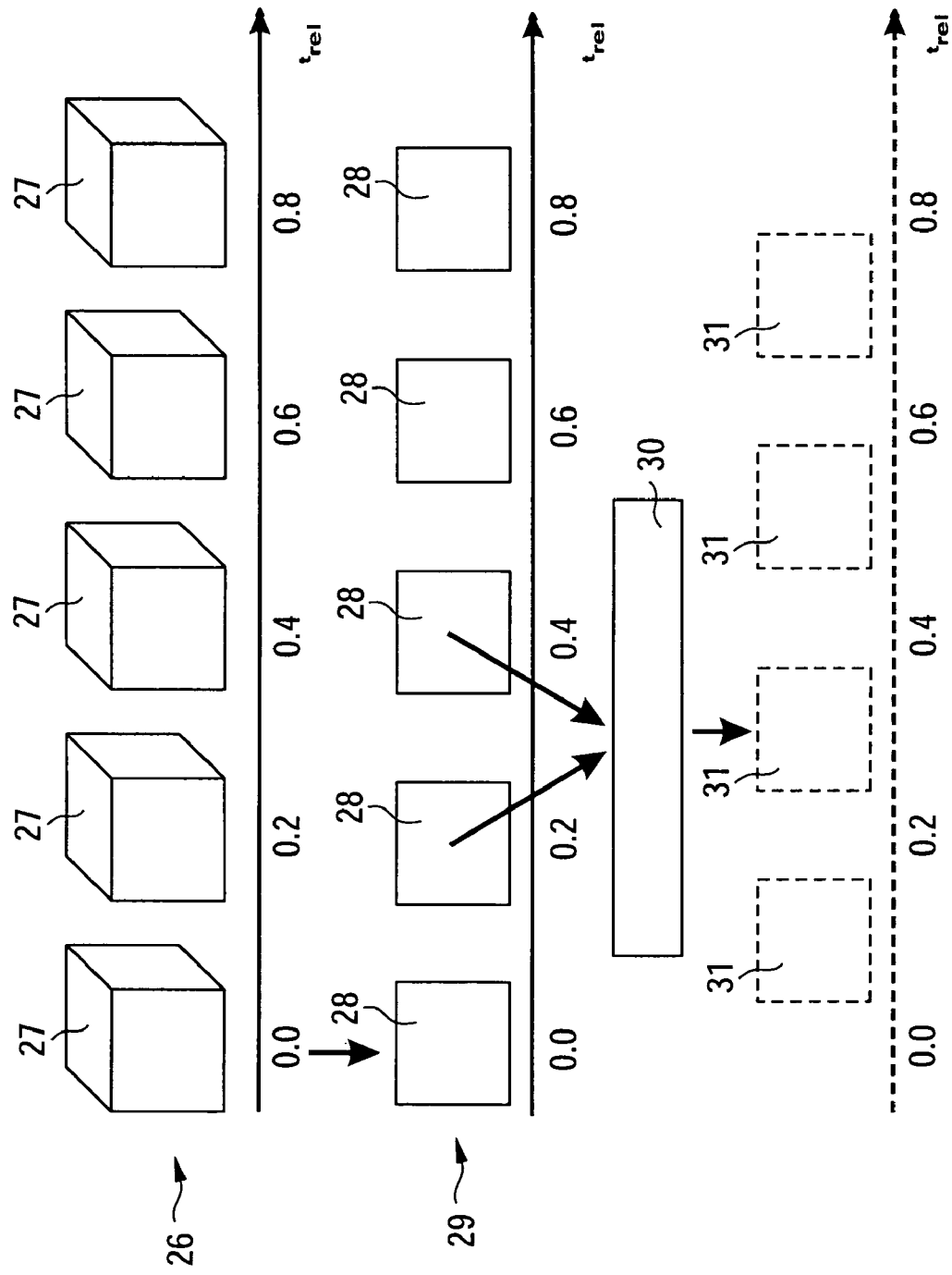
FIG. 5 shows a diagram illustrating the sequence of the data reduction carried out by the evaluation unit of the angiography device.

As a result, the modelator 14 generates a four-dimensional data set 26, as displayed in FIG. 5, said data set having a plurality of models 27 of the heart assigned to various time points $t_{rel}$.

The movement analyzer 15 mentioned in relation to FIG. 3 generates model projection images 28 at various projection angles θ, with the aid of model 27. To create the model projection images 28, methods known to a person skilled in the art, for example referred to as DRR (digitally reconstructed radiograph) or MIP (maximum intensity projection) are used.

A three-dimensional data set 29 is shown in FIG. 5, which has model projection images 28 assigned to a specific projection angle θ at various relative times $t_{rel}$.

The movement analyzer 15 now calculates movement fields 31 in an analysis process 30, said movement fields describing the movement of the image structures in the two-dimensional model projection images 28. In this way for example, search algorithms which are used in conjunction with the video coding can be accessed.

Figure 6:
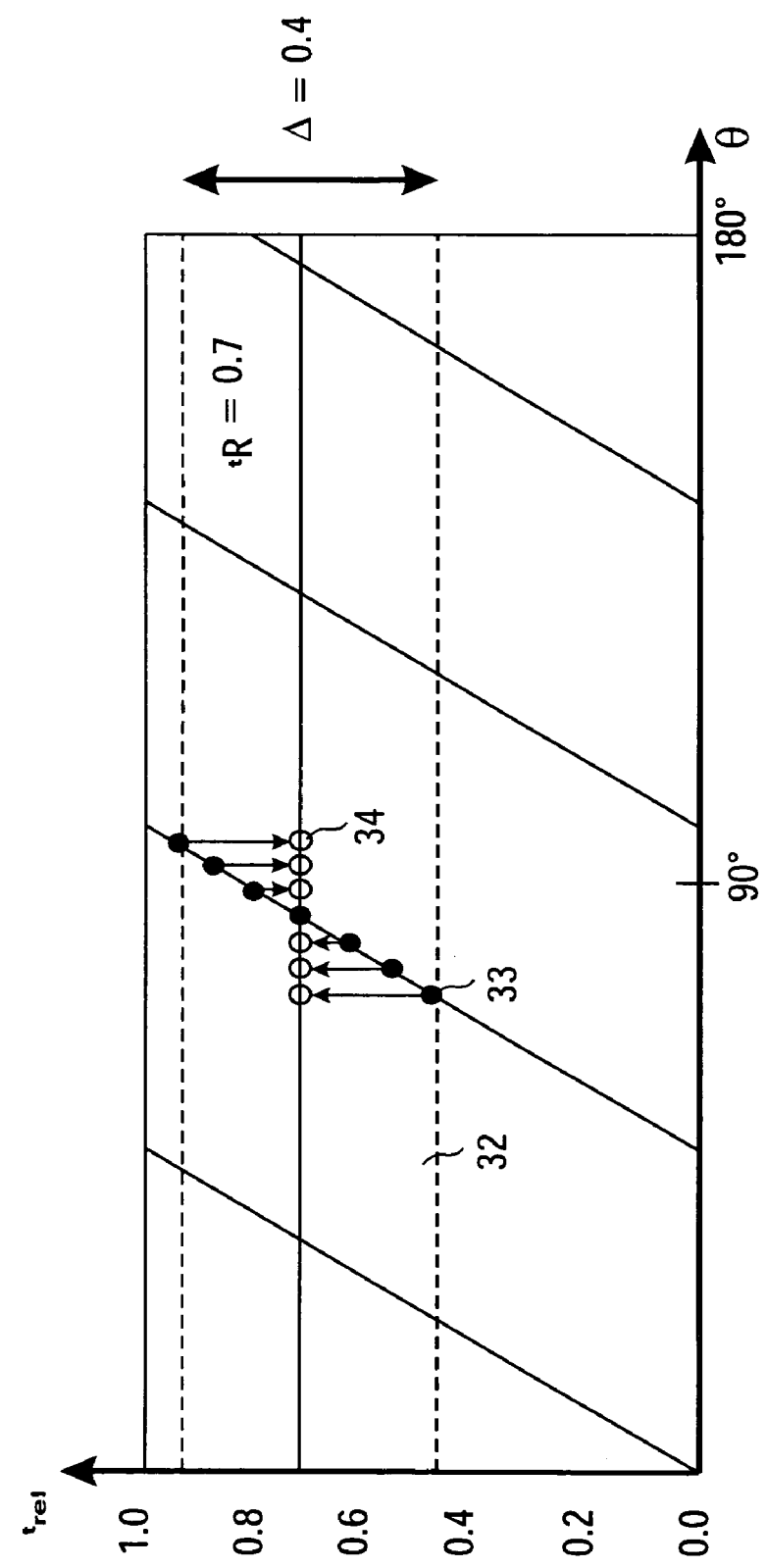
FIG. 6 shows a diagram displaying the phase location of the originally recorded projection images and the phase angle of the movement-corrected projection images in relation to the projection angle of the angiography device and the relative time of a heart cycle.

After the movement fields 31 have been obtained, the movement compensator 16 performs a movement compensation of the type illustrated in FIG. 6. FIG. 6 displays phase angles 33 of projection images in a time frame 32, said phase angles being assigned to the time frame 32. The original phase angles 33 are conveyed to the corrected phase angles 34 with the aid of the movement compensator 16, so that each projection image corresponds to the associated corrected projection images which are recorded at a fixed time $t_{rel}$ and at different projection angles θ. The generation of movement-compensated projection images at time point $t_{rel}$=0.7 is illustrated for example in FIG. 4, said projection images being used whose phase angles 33 is located within a time frame 32 of the width Δ=0.4.

The projection images movement-compensated in this manner are finally fed to the reconstruction unit 17, which generates the structure data of the heart of a patient 2 from the movement-compensated projection images.

As already mentioned, the structure data can also be three-dimensional models of the heart of a patient 2 associated with various relative times $t_{rel}$, from which the movement analyzer 15 can calculate refined movement fields 31, so that refined structure data sets result with an iteration of the method carried out by the evaluation unit 8, which can again be fed to the movement analyzer until the structure data sets no longer change or change only slightly.

It should be noted that the evaluation of the heart signal of the electrocardiograph 11 is not necessary in each case. In fact, the heart cycles 23 can also be approximately estimated from the original projection images.

Furthermore, it should be noted that the device described here can essentially also be used for examining objects not moving cyclically.

Finally please note that terms such as modelator, movement analyzer, movement compensator or reconstruction units are to be understood as functional. These logical units do not necessarily have to form physical units, but can also be realized in a physical unit in the form of software and conversely distributed over a plurality of physical units.

The invention claimed is:

1. A device for obtaining structural data of a moving object, comprising:
   a radiation source configured to be moved around the object along a measuring path;
   a detector arranged on an opposite side of the object relative to the radiation source for generating a plurality of projection images of the object, the detector configured to be moved based on the movement of the radiation source;
   a modeling unit for determining a plurality of object models of the object using the projection images corresponding to a plurality of time frames; wherein each object model of the plurality of object models is determined using a plurality of projection images per cycle of the moving object, wherein each object model corresponds to a different time frame, and wherein each time frame comprises a plurality of cycles of the moving object;
   a movement analyzing unit for determining model projection images for various projection angles based on the object models and for determining movement fields for the projection images using the model projection images assigned to a projection angle at various relative times;
   a movement compensating unit for calculating movement-corrected projection images based on the movement fields, wherein said movement-corrected projection images are recorded at a fixed relative time and at different projection angles; and
   a reconstruction unit for calculating the structural data of the object using the movement-corrected projection images.

2. The device according to claim 1, further comprising a plurality of movement detecting sensors for determining the structural data of the object having a cyclic movement.

3. The device according to claim 2, wherein the movement detecting sensors are configured and arranged to determine a movement cycle corresponding to the cyclic movement of the object.

4. The device according to claim 2, further comprising an electro-cardiograph for determining the structural data of a beating heart.

5. The device according to claim 1, wherein the structural data include a plurality of structural data sets corresponding to a plurality of movement phases, and the movement analyzing unit determines refined movement fields based on the structural data sets.

6. The device according to claim 5, wherein the structural data sets are refined using the refined movement fields.

7. The device according to claim 3, wherein the movement cycle is calculated based on the projection images acquired by the detector.

8. The device according to claim 1, wherein the radiation source is an X-ray source and the detector is an X-ray detector.

* * * * *